(12) United States Patent
Mathaneswaran et al.

(10) Patent No.: US 11,705,020 B2
(45) Date of Patent: Jul. 18, 2023

(54) METHOD OF MANUFACTURING A BIO-MODEL COMPRISING A SYNTHETIC SKIN LAYER AND BIO-MODEL COMPRISING A SYNTHETIC SKIN LAYER

(71) Applicant: UNIVERSITI MALAYA, Kuala Lumpur (MY)

(72) Inventors: Vickneswaran A/L Mathaneswaran, Kuala Lumpur (MY); Zainal Ariff Bin Abdul Rahman, Kuala Lumpur (MY); Yuwaraj Kumar A/L Balakrishnan, Kuala Lumpur (MY); Su Tung Tan, Kuala Lumpur (MY)

(73) Assignee: UNIVERSITI MALAYA, Kuala Lumpur (MY)

( * ) Notice: Subject to any disclaimer, the term of this patent is extended or adjusted under 35 U.S.C. 154(b) by 1216 days.

(21) Appl. No.: 16/317,540

(22) PCT Filed: Jul. 12, 2017

(86) PCT No.: PCT/MY2017/050037
§ 371 (c)(1),
(2) Date: Jan. 12, 2019

(87) PCT Pub. No.: WO2018/012960
PCT Pub. Date: Jan. 18, 2018

(65) Prior Publication Data
US 2019/0220974 A1    Jul. 18, 2019

(30) Foreign Application Priority Data
Jul. 12, 2016  (MY) ............................... 2016001297

(51) Int. Cl.
*G09B 23/30*  (2006.01)
*B33Y 80/00*  (2015.01)
(Continued)

(52) U.S. Cl.
CPC .............. *G09B 23/30* (2013.01); *A61B 34/10* (2016.02); *B33Y 50/00* (2014.12); *B33Y 80/00* (2014.12);
(Continued)

(58) Field of Classification Search
CPC ............................... G09B 23/28; G09B 23/30
See application file for complete search history.

(56) References Cited

U.S. PATENT DOCUMENTS 8,105,089 B2 *  1/2012  Hudson ................. G09B 23/34
                                                       434/274
8,915,743 B2 * 12/2014  Meglan ................ G09B 23/283
                                                       434/262
9,017,080 B1 *  4/2015  Placik .................. G09B 23/285
                                                       434/269

(Continued)

OTHER PUBLICATIONS

International Search Report and Written Opinion of International Search Authority for International Application No. PCT/MY2017/050037.

*Primary Examiner* — Kurt Fernstrom
(74) *Attorney, Agent, or Firm* — Preston Smirman; Smirman IP Law, PLLC

(57) ABSTRACT

A method of manufacturing a three dimensional bio-model from medical image data is described. The method comprises: identifying a skin layer in the medical image data; determining a thickness of the skin layer; generating three dimensional model data from the medical image data, the three dimensional model data comprising an indication of a synthetic skin layer, the synthetic skin layer comprising a surface layer and a backing layer, wherein a combined thickness of the surface layer and the backing layer is determined from the thickness of the skin layer; and three dimensional printing the three dimensional model data to provide a three dimensional bio-model.

8 Claims, 3 Drawing Sheets

(51) Int. Cl.
*A61B 34/10* (2016.01)
*B33Y 50/00* (2015.01)
*G16H 50/50* (2018.01)
*G06T 7/00* (2017.01)

(52) U.S. Cl.
CPC ............ *G06T 7/0012* (2013.01); *G16H 50/50* (2018.01); *A61B 2034/101* (2016.02)

(56) References Cited

U.S. PATENT DOCUMENTS

| | | | | |
|---|---|---|---|---|
| 10,181,270 | B1* | 1/2019 | Fuller | G09B 23/30 |
| 10,359,348 | B1* | 7/2019 | Lytle | G01L 5/0052 |
| 2004/0145627 | A1* | 7/2004 | Silverbrook | H05K 3/125 |
| | | | | 347/40 |
| 2005/0026125 | A1 | 2/2005 | Toly | |
| 2009/0149977 | A1* | 6/2009 | Schendel | G16H 50/50 |
| | | | | 700/98 |
| 2010/0167254 | A1* | 7/2010 | Nguyen | G09B 23/30 |
| | | | | 434/272 |
| 2012/0308805 | A1* | 12/2012 | Sella | B29C 64/112 |
| | | | | 428/222 |
| 2014/0038153 | A1* | 2/2014 | Courtoy | G09B 23/30 |
| | | | | 434/271 |
| 2014/0212864 | A1 | 7/2014 | Rios et al. | |
| 2014/0370475 | A1* | 12/2014 | Bova | G09B 23/285 |
| | | | | 434/267 |
| 2015/0352250 | A1* | 12/2015 | Dalman | A61F 2/28 |
| | | | | 523/115 |
| 2016/0027341 | A1* | 1/2016 | Kerins | G09B 23/30 |
| | | | | 264/28 |
| 2016/0039120 | A1* | 2/2016 | Dikovsky | B29C 33/40 |
| | | | | 264/129 |
| 2016/0287339 | A1* | 10/2016 | Bin Abdul Rahman | |
| | | | | A61B 8/00 |
| 2017/0360578 | A1* | 12/2017 | Shin | G09B 23/286 |
| 2019/0021865 | A1* | 1/2019 | Vogtmeier | A61F 2/30942 |
| 2019/0090824 | A1* | 3/2019 | Brunicardi | G06T 15/06 |

* cited by examiner

METHOD OF MANUFACTURING A BIO-MODEL COMPRISING A SYNTHETIC SKIN LAYER AND BIO-MODEL COMPRISING A SYNTHETIC SKIN LAYER

FIELD OF THE INVENTION

Embodiments of the present invention relate to three dimensional bio-models for use in simulating or practicing surgical procedures, and in particular to bio-models comprising a synthetic skin layer; and the manufacture of such bio-models.

BACKGROUND OF THE INVENTION

Surgery is a difficult discipline to master. In order to develop and perfect their surgical skills, trainees and junior surgeons must repeatedly practice surgical procedures. Traditionally trainee surgeons have used cadavers to develop and practice their technique. The use of cadavers presents a number of issues: in many countries the use of cadavers is restricted for ethical and religious reasons; and the cost associated with preservation and disposal of is high. Further, in order to simulate many medical procedures an accurate representation of a specific pathology is required. An example of this is the simulation of the procedure required for the removal of a tumor. In such a case, the position, orientation, size and nature of the tumor will be unique to the pathology of a specific patient. Therefore a simulation based on a normal anatomy without the tumor will be of little or no benefit in for a surgeon preparing for the removal of a tumor.

Recent developments in three-dimensional printing techniques allow the production of three-dimensional bio-models of parts of the human anatomy which can assist surgeons in practicing their technique. The production of bio-models by these techniques allows accurate representations of the human body to be produced. The bio-models may be based on a specific patient and include accurate representations of the anatomy specific to that patient. Surgeons may use such bio-models to simulate and plan surgeries for specific patients as well as to practice general surgical techniques. In addition to accurately reproducing the anatomy of a patient, such bio-models must also accurately reproduce the response of a real anatomy to surgical tools.

SUMMARY OF THE INVENTION

According to a first aspect of the present invention there is provided method of manufacturing a three dimensional bio-model from medical image data. The method comprises: identifying a skin layer in the medical image data; determining a thickness of the skin layer; generating three dimensional mod& data from the medical image data, the three dimensional mod& data comprising an indication of a synthetic skin layer, the synthetic skin layer comprising a surface layer and a backing layer, wherein a combined thickness of the surface layer and the backing layer is determined from the thickness of the skin layer; and three dimensional printing the three dimensional model data to provide a three dimensional bio-model.

In embodiments of the present invention, the synthetic skin layer of the bio-model has a thickness that corresponds to the medical image data. This means that the bio-model accurately mimics the patient from which the medical image data was derived. The synthetic skin layer is formed from two layers: the surface layer and the backing layer. The surface layer may have a constant thickness across different parts of the bio-model. By keeping the thickness of the surface layer approximately constant, the properties of the skin layer such as flexibility and strength can be matched to the properties of real skin. The backing layer has a varying thickness. By varying the thickness of the backing layer, the combined thickness of the synthetic skin layer can be controlled to match the thickness of the skin layer in the medical image data.

In an embodiment, the surface layer has a thickness greater than 0.2 mm. It has been found that a thickness of greater than 0.2 mm for the surface layer results in the synthetic skin layer being strong enough to hold sutures.

In an embodiment, the surface layer has a thickness of less than 2 mm. It has been found that a thickness of less than 2 mm for the for the surface layer results in the synthetic skin layer having a flexibility that mimics the flexibility of real skin.

The bio-model may have a synthetic bone layer under the synthetic skin layer. The synthetic bone layer may be a synthetic skull layer.

The backing layer may be 3D printed over the synthetic skull layer to mimic the peeling properties of human anatomy.

The bio-model may further comprise a synthetic anatomical structure under the synthetic skin layer. The synthetic anatomical structure may be for example, a tumor.

The method may involve a user inputting an indication identifying the skin layer in the medical image data.

According to a second aspect of the present invention there is provided a three dimensional bio-model for simulating a simulated surgical procedure. The bio-model comprises a synthetic bone layer; and a synthetic skin layer over the synthetic bone layer, the synthetic skin layer comprising a surface layer and a backing layer.

In an embodiment the three dimensional bio-model is configured to be insertable into a slot in a base piece.

In an embodiment the three dimensional bio-model comprises a base piece and an insert, the base piece defining a slot, the insert being configured to fit into the slot, the insert comprising the synthetic bone layer; and the synthetic skin layer.

The insert provides an accurate representation of the internal anatomy which may be cut or otherwise changed during a simulated procedure. Therefore, the insert can only be used for one simulated procedure. Since the base part is not altered during a simulated procedure it can be reused. Therefore only the insert is discarded following a simulated procedure. This reduces the cost of each individual simulation since only the insert must be replaced.

The surface of the base part may accurately represent the surface of a part of a body such as a head. This allows surgical navigation systems to be used during the simulated surgical procedure. Surgical navigation systems such as the Medtronic StealthStation S7 System use optical navigation cameras to assist a surgeon during surgery. The provision of a base part which accurately reproduces the surface features in an area around the simulated procedure location allows the use of the navigation system to be incorporated in the simulation of the surgical procedure.

Alternatively, the three dimensional bio-model may be produced as a single part.

BRIEF DESCRIPTION OF THE DRAWINGS

In the following, embodiments of the present invention will be described as non-limiting examples with reference to the accompanying drawings in which.

DETAILED DESCRIPTION

Figure 1:
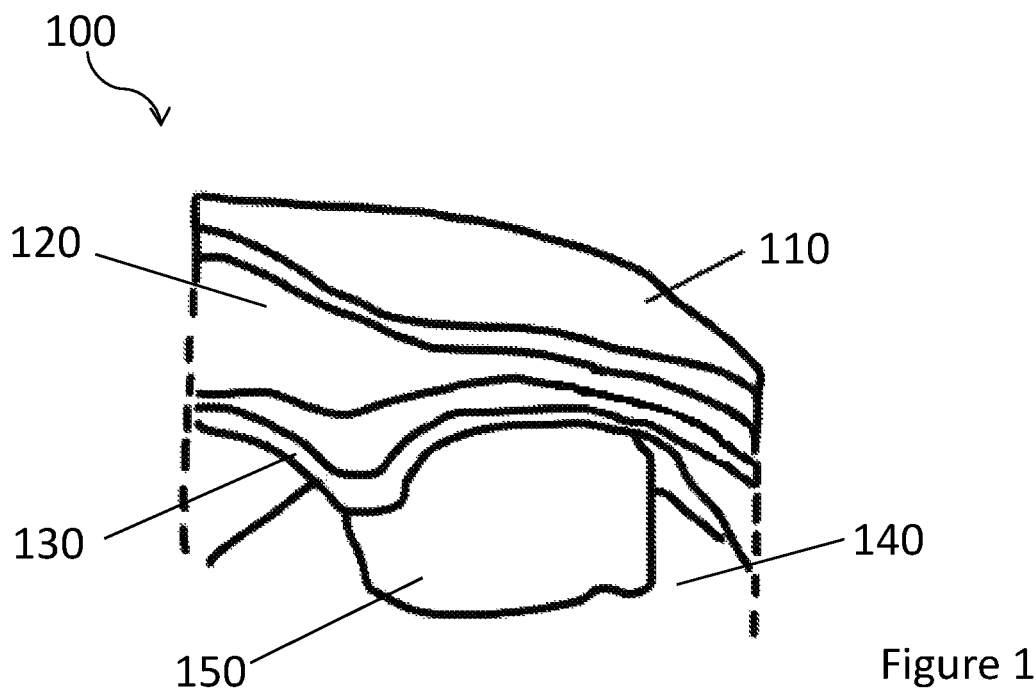
FIG. 1 shows a bio-model according to an embodiment of the present invention.

FIG. 1 shows a bio-model according to an embodiment of the present invention. The bio-model 100 in this example is a cranial bio-model and mimics the anatomy of part of a human head. The bio-model 100 comprises a synthetic skin layer 110. Under the synthetic skin layer 110 there is a synthetic skull layer 120. There is a synthetic dura layer 130 below the synthetic skull layer 120. The synthetic dura layer 140 covers a synthetic brain tissue 140. A synthetic tumor 150 is located in the synthetic brain tissue 140.

The bio-model 100 is used to simulate a surgical procedure. The simulation of a surgical procedure will typically involve making an incision through the synthetic skin layer 110. In order to accurately reproduce the experience of real surgery for the trainee surgeon or person carrying out the simulated surgical procedure, the synthetic skin layer must accurately reproduce the properties of a real skin layer. For example the simulated surgical procedure may involve techniques or steps to peel the synthetic skin and also use surgical tool to operate on the synthetic skin layer. For example a scalpel may be used to cut the synthetic skin layer and then a retractor may be used to peel the synthetic skin layer from the synthetic bone layer of the bio-model.

The bio-model 100 is a direct representation of a human patient head based on medical data obtained from relevant medical scanning technology. The bio-model 100 represents a region of interest based on the pathological finding from the medical data obtained. The location and the size, which included length, width and depth of the skin is dependent on the location of interest set and based on the pathological finding obtained.

The bio-model 100 can be produced with material such as powder substance by any rapid prototyping technology such as additive manufacturing technology, 3D printer and laser sintering or any other manufacturing process such as casting, moulding and injection model, however for the synthetic skin layer 110 the structure of the skin layer can be produced accordingly to directly represent the real anatomy. Multiple material include PVC rubber, silicone, polymeric material or any two or more combination thereof can be used to fabricate structure according to the real anatomy in term of the look and feel same like real human skin.

Figure 2:
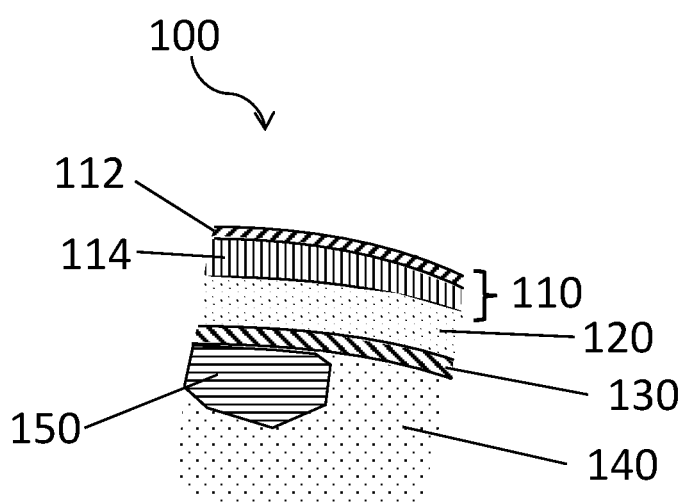
FIG. 2 shows a cross section through a bio-model according to an embodiment of the present invention.

FIG. 2 shows a cross cross section through a bio-model according to an embodiment of the present invention. As shown in FIG. 2, the synthetic skin layer 110 comprises a surface layer 112 and a backing layer 114. Under the synthetic skin layer 110 there is a synthetic skull layer 120. There is a synthetic dura layer 130 under the synthetic skull layer 120. A synthetic tissue layer 140 is located under the synthetic dura layer 130. The synthetic tissue layer 140 includes a synthetic tumor 150.

It will be appreciated that while the bio-model 100 shown in FIGS. 1 and 2 is a cranial bio-model representing a part of a human head, the synthetic skin layer described herein may be applied to bio-models representing other parts of the human anatomy. The skin can be located anywhere with regard to the patient case and the pathological finding obtain.

In an embodiment, the thickness of the surface layer is 0.5 mm. It has been found that this thickness allows the skin layer to have a flexibility which matches the flexibility of true skin and also allows the synthetic skin layer to take sutures. If the surface layer is less than 0.2 mm thick it becomes too weak to support a suture. If the surface layer is greater than 2 mm thick then synthetic skin layer becomes too rigid to accurately simulate the properties of human skin.

The synthetic skin layer is typically between 2 mm and 4 mm thick. The surface layer and the backing layer may be formed from a rubber like material such as TangoPlus from Stratsys.

In an embodiment, the bio-model is an insert which fits into a slot in a base piece. This is shown in FIG. 3.

Figure 3:
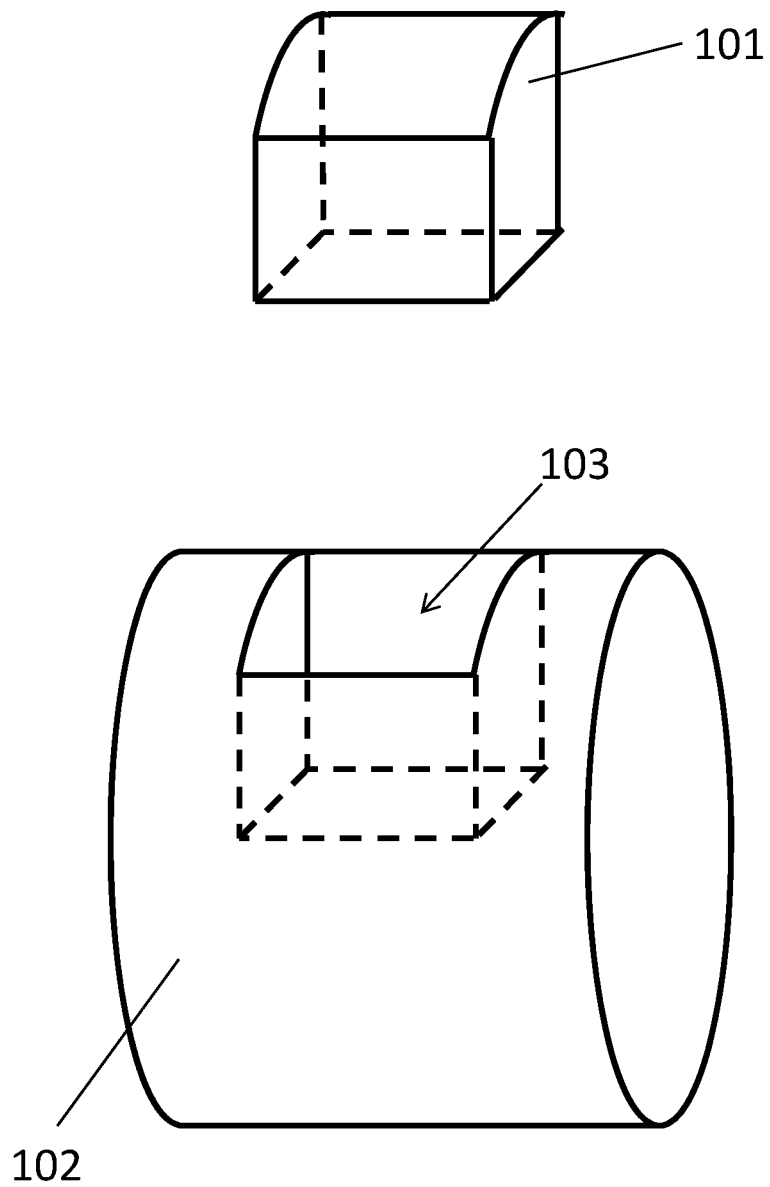
FIG. 3 shows a bio-model which comprises an insert according to an embodiment of the present invention.

FIG. 3 shows a cranial bio-model according to an embodiment of the present invention which comprises a base piece and an insert. The insert 101 is as described above in relation to FIGS. 1 and 2. The sides of the insert may be formed as walls. The base piece 102 has a slot 103 into which the insert 101 can be fitted.

The exterior surface of the base piece 102 has contours and features which correspond to the exterior of part of the head. For example, the base piece may include the contours and features of a human head or the facial features of a human head.

While the exterior of the base piece 102 is shaped to simulate the corresponding parts of the human anatomy, the interior structure is not. The interior of the base piece 102 may be solid or hollow. During a simulated surgical procedure the insert 101 provides a simulation of the interior structure of the body being operated on. The base piece 102 provides a simulation of the exterior of the patient.

During many surgical procedures, surgical navigation systems are used by the surgeon for guidance. An example of a surgical navigation system is the Medtronic StealthStation S7 System. Such navigation systems use optical navigation to determine locations on a patient's body. The base piece 102 and insert 101 may be produced using scan data from a patient as described below with reference to FIG. 4 in more detail. Since the exterior surface of the base piece 102 will correspond to this scan data, the base piece 102 provides an accurate simulation of the surgical procedure using the navigation system.

The insert 101 includes a top layer of synthetic skin to simulate the skin of the patient during the simulated surgical procedure. During simulation of the surgical procedure, the surgeon will cut an incision or insert a probe through this skin layer. In addition, the surgeon may cut or alter the internal structure of the insert 101. Therefore, the insert 101 can normally only be used for one simulated surgical procedure and is then discarded. Since no changes are made to the base piece 102, it can be reused when the simulation is repeated, for example if the surgeon wishes to practice the same procedure a number of times or to alter certain aspects during planning of a surgical procedure. Therefore the amount of the model which is discarded can be reduced by providing a base piece which can be reused.

Figure 4:
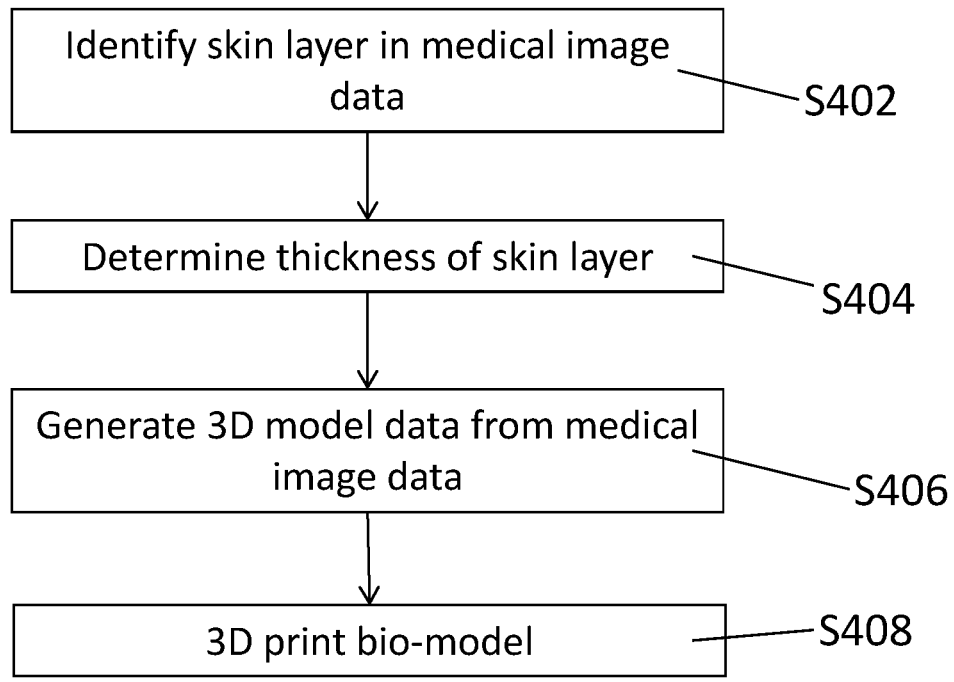
FIG. 4 is a flow chart showing a method of manufacturing a bio-model according to an embodiment of the present invention.

FIG. 4 is a flow chart showing a method of manufacturing a bio-model according to an embodiment of the present invention. The method shown in FIG. 4 may be carried out using a computer and a three dimensional printer.

The method involves the process of outlining the skin layers and determining the layers by the use of computer assisted design (CAD) software. The layers may be predetermined through one or combination of medical data that was obtained by using medical scanning technology such as Computed Tomography (CT) Scan and Magnetic Resonance Imaging (MRI). Since, medical scanning images come in form of slices, the skin layers were outline on each of the slices before reconstruction was done.

The reconstruction of the image is done by stacking all the respective slices which then indirectly form a 3D image made of slices of images. From this onwards, the 3D images is screened and cleaned before converting into a 3D format image.

The 3D image of the present invention is then printed with 3D printer to produce a 3D physical model of the image. With multi-material printer capability, each of the layer can be printed with one or combination two or more materials. The material constituents can be adjusted to achieve the closest consistency, elasticity and rigidity in comparison to the real anatomy.

Medical image data for a region of a patient is received the computer. The medical image data may be stored data obtained from a medical imaging apparatus such as a magnetic resonance imaging (MRI) apparatus, a computed tomography (CT) apparatus, an X-ray imaging apparatus, or an ultrasound imaging apparatus. The medical image data may be in the Digital Imaging and Communications (DI-COM) format.

In step S402, a skin layer is identified in the medical image data. This identification may be made by an operator, or the skin layer may be automatically using image processing software. The medical image data may be segmented, that is, the various layers and tissues in the images may be labelled. This labelling may be implemented automatically using image analysis, or the images may be segmented manually by an operator.

In step S404, the thickness of the skin layer is determined from the medical image data.

In step S406 three dimensional model data is generated using a 3D conversion algorithm which generates three dimensional surfaces from the medical image data. Algorithms such as the marching cube algorithm, Delaunay's triangulation algorithm or a combination of the two may be used. The result of step S406 is a three dimensional model of the region of the patient. The three dimensional mod& data comprises an indication of a synthetic skin layer which comprises a surface layer and a backing layer. The combined thickness of the surface layer and the backing layer is determined from the thickness of the skin layer from the determined in step S404. The thickness of the surface layer may be fixed by the desired properties and the thickness of the backing layer set so that the total thickness of the synthetic skin layer matches the thickness of the skin layer.

In step S406, the bio-model 100 is printed using three dimensional printing. The shape of the structures and materials to be used for each anatomical region can be predetermined in the 3D data. By this way of predetermination and modification, accurate shape and material can be assigned to each anatomical region, beneficial specifically for pre-surgical training, surgical simulation and surgical training.

The layers of the synthetic skin layer are printing all at once through a multi-material 3d printer. As described above, the materials are selected to reproduce a layer having a consistency and response close to that of an actual human skin layer. This involves selecting the combination of materials to produce a variation of the structures rigidity and elasticity.

The synthetic skin layer 110 may be fabricated simultaneously with the rest of the bio-model, or separately in depending on the size or type of the pathology present.

In an embodiment, the 3D data is subjected to a rapid additive manufacturing technique where layers of material are added upon one another to form the 3D anatomical structure. The rapid additive manufacturing techniques used to produce the bio-model 100 may include layered manufacturing, direct digital manufacturing, laser processing, electron beam melting, aerosol jetting, inkjet printing or semi-solid free-form fabrication. The 3D data enables the rapid additive manufacturing machine to sequentially build up many thin layers upon another to build the 3D bio-model.

In embodiments of the invention, the multiple choices of materials are used to fabricate the bio-model and the synthetic skin layer. The bio-model 100 can be produced with material such as powder substance by any rapid prototyping technology such as additive manufacturing technology, 3D printer and laser sintering or any other manufacturing process such as casting, moulding and injection model, however for the synthetic skin layer the structure of the skin layer can be produced accordingly to directly represent the real anatomy. Multiple material include PVC rubber, silicone, polymeric material or any two or more combination thereof can be used to fabricate structure according to the real anatomy in term of the look and feel same like real human skin.

As described above, embodiments of the present invention provide a bio-model which accurately simulates the response of the skin to surgical procedures. The bio-model is produced using medical image data and there provides a 3D model that accurately simulates the actual anatomical structure. The 3D model represents the selected structures, organs or any region of interest and pathology of the disease.

Embodiments of the present invention provide an accurate anatomical model which serves as tool for a better understanding on the condition of a patient or the procedure for operating on a patient.

As described above, embodiments of the present invention provide a method of mimicking the human skin, which accurately simulates the actual human tissue which is present on a human patient.

Whilst the foregoing description has described exemplary embodiments, it will be understood by those skilled in the art that many variations of the embodiment can be made within the scope and spirit of the present invention.

The invention claimed is:

1. A method of manufacturing a three dimensional bio-model from medical image data, comprising:
   identifying a skin layer in the medical image data;
   determining a thickness of the skin layer;
   generating three dimensional model data from the medical image data, the three dimensional model data comprising an indication of a synthetic skin layer, the synthetic skin layer comprising a surface layer and a backing layer;
   three dimensional printing layers of the synthetic skin layer at once based on the three dimensional model data;
   fabricating a synthetic bone layer and synthetic dura layer in which the synthetic bone layer is disposed in-between the synthetic skin layer and the synthetic dura layer for forming an insert; and
   fabricating a base piece based on the medical image data;
   wherein the insert and the base piece define the three dimensional bio-model in which the insert has sides formed with walls for it to be detachably fitted into a slot defined on the base piece.

2. The method according to claim 1, wherein the surface layer has a thickness greater than 0.2 mm.

3. The method according to claim 1, wherein the surface layer has a thickness less than 2 mm.

4. The method according to claim 1, wherein the three dimensional model data further comprises an indication of the synthetic bone layer under the synthetic skin layer.

5. The method according to claim 4, wherein the synthetic bone layer is a synthetic skull layer.

6. The method according to claim 5, wherein the backing layer of the synthetic skin layer is three dimensional printed over the synthetic skull layer such that the synthetic skin layer can be peeled from the synthetic skull layer.

7. The method according to claim 1, wherein the three dimensional model data further comprises an indication of a synthetic tumor layer under the synthetic skin layer.

8. The method according to claim 1, wherein the step of identifying a skin layer in the medical image data further comprises the step of receiving a user input indicating the skin layer.

\* \* \* \* \*